(12) United States Patent
Hagiya et al.

(10) Patent No.: US 8,604,221 B2
(45) Date of Patent: Dec. 10, 2013

(54) PRODUCTION METHOD OF HALOGEN-SUBSTITUTED PHTHALIDE

(75) Inventors: Koji Hagiya, Ibaraki (JP); Yasutaka Aoyagi, Yokohama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/265,699

(22) PCT Filed: May 19, 2010

(86) PCT No.: PCT/JP2010/058858
§ 371 (c)(1),
(2), (4) Date: Nov. 1, 2011

(87) PCT Pub. No.: WO2010/134630
PCT Pub. Date: Nov. 25, 2010

(65) Prior Publication Data
US 2012/0142946 A1    Jun. 7, 2012

(30) Foreign Application Priority Data

May 21, 2009   (JP) .................. 2009-122909
Jun. 30, 2009   (JP) .................. 2009-154752

(51) Int. Cl.
*C07D 305/12* (2006.01)

(52) U.S. Cl.
USPC ........................................... 549/307

(58) Field of Classification Search
USPC ........................................... 549/307
See application file for complete search history.

(56) References Cited

U.S. PATENT DOCUMENTS 5,364,876 A * 11/1994 Hamilton ............... 514/381

FOREIGN PATENT DOCUMENTS

| JP | 46-015094 B | 4/1971 | | |
|---|---|---|---|---|
| WO | 2004089897 A1 | 10/2004 | | |
| WO | 2004089924 A1 | 10/2004 | | |
| WO | WO 2004/089924 | * 10/2004 | ........... | C07D 307/88 |
| WO | 2005073205 A1 | 8/2005 | | |

OTHER PUBLICATIONS

Parrini, Gazzetta Chimica Italiana, 1957, vol. 87, pp. 1147-1162. Oct. 2004.*
Narasimhan, Heterocycles, 1982, 18, 131-5.*
Saucy et al. Journal of Organic Chemistry, 1987, vol. 52, No. 1, pp. 129-134.*
Int'l Preliminary Report on Patentability issued Dec. 22, 2011 in Int'l Application No. PCT/JP2010/058858.
Int'l Search Report issued Sep. 7, 2010 in Int'l Application No. PCT/JP2010/058858.
Parrini, "Lithium aluminum hydride reduction of phthalic, cyclohexene-1,2-dicarboxylic, and cyclohexane-1,2-dicarboxylic anhydrides," Gazzetta Chimica Italiana, vol. 87, pp. 1147-1162 (1957).
Soucy et al, "On the Regioselectivity of Metal Hydride Reductions of 3-Substituted Phthalic Anhydrides," Journal of Organic Chemisty, vol. 52, No. 1, pp. 129-134 (1987).
Supplementary European Search Report issued Sep. 12, 2012 in EP Application No. 10777857.3.
Kayser et al, "Regioselectivity of metal hydride reductions of unsymmetrically substituted cyclic anhydrides. Systems where 'steric hindrance along the preferred reaction path' rationalization is not applicable", Canadian Journal of Chemistry, vol. 58, pp. 2484-2490 (1980).
Narasimhan, "Improved Procedure for Lithium Borohydride Reduction of Cyclic Anhydrides to Lactones in Tetrahydrofuran", Heterocycles, vol. 18, pp. 131-135 (1982).
Zhou et al, "Synthesis and SAR of Novel Di- and Trisubstituted 1,4-Dihydroquinoxaline-2,3-diones Related to Licostinel (Acea 1021) as NMDA/Glycine Site Antagonists", Bioorganic & Medicinal Chemistry, vol. 11, pp. 1769-1780 (2003).

* cited by examiner

*Primary Examiner* — Nizal Chandrakumar
(74) *Attorney, Agent, or Firm* — Panitch Schwarze Belisario & Nadel LLP

(57) ABSTRACT

Disclosed is a method for producing a halogen-substituted phthalide, which includes a reaction step of reacting a halogen-substituted phthalic anhydride with sodium borohydride.

5 Claims, No Drawings

PRODUCTION METHOD OF HALOGEN-SUBSTITUTED PHTHALIDE

CROSS-REFERENCE TO RELATED APPLICATION

This application is a Section 371 of International Application No. PCT/JP2010/058858, filed May 19, 2010, which was published in the Japanese language on Nov. 25, 2010, under International Publication No. WO 2010/134630 A1, and the disclosure of which is incorporated herein by reference.

TECHNICAL FIELD

The present invention relates to a method for producing a halogen-substituted phthalide.

BACKGROUND ART

A halogen-substituted phthalide is, for example, an important compound as a raw material, an intermediate and a bulk of pharmaceuticals and pesticides. Particularly, 4,5,6,7-tetrachloro-1(3H)-isobenzofuranone (another name: 4,5,6,7-tetrachlorophthalide) is widely known as a bactericide for rice blast (see, for example, JP-B-46-15094).

Gazzetta Chimica Italiana, 87, p. 1147 (1957) describes, as a method for producing a halogen-substituted phthalide, for example, a method in which tetrachlorophthalic anhydride is reacted with lithium aluminum hydride to obtain 4,5,6,7-tetrachloro-1(3H)-isobenzofuranone.

DISCLOSURE OF THE INVENTION

The present invention relates to a novel method for producing a halogen-substituted phthalide.

That is, the present application relates to the following inventions:
[1] a method for producing a halogen-substituted phthalide, which includes a reaction step of reacting a halogen-substituted phthalic anhydride with sodium borohydride;
[2] the method according to [1], wherein the reaction step is performed in the presence of at least one solvent selected from the group consisting of ether solvents and alcohol solvents;
[3] the method according to [1] or [2], which further includes a mixing step of mixing the reaction mixture obtained in the reaction step with an acid;
[4] the method according to [3], wherein the acid is an inorganic acid;
[5] the method according to [3], wherein the acid is hydrogen chloride; and
[6] the method according to any one of [1] to [5], wherein the halogen-substituted phthalic anhydride is tetrachlorophthalic anhydride and the halogen-substituted phthalide is 4,5,6,7-tetrachloro-1(3H)-isobenzofuranone.

MODE FOR CARRYING OUT THE INVENTION

The present invention will be described in detail below.

In the present invention, the halogen-substituted phthalic anhydride is phthalic anhydride in which at least one of four hydrogen atoms contained in phthalic anhydride is substituted with a halogen atom such as a fluorine atom, a chlorine atom or a bromine atom. Examples of the halogen-substituted phthalic anhydride include monohalogen-substituted phthalic anhydride, dihalogen-substituted phthalic anhydride, trihalogen-substituted phthalic anhydride and tetrahalogen-substituted phthalic anhydride.

The monohalogen-substituted phthalic anhydride is phthalic anhydride in which one of four hydrogen atoms contained in phthalic anhydride is substituted with a halogen atom.

Examples of the monohalogen-substituted phthalic anhydride include 3-fluorophthalic anhydride, 4-fluorophthalic anhydride, 3-chlorophthalic anhydride, 4-chlorophthalic anhydride, 3-bromophthalic anhydride and 4-bromophthalic anhydride.

The dihalogen-substituted phthalic anhydride is phthalic anhydride in which two hydrogen atoms of four hydrogen atoms contained in phthalic anhydride are substituted with a halogen atom.

Examples of the dihalogen-substituted phthalic anhydride include 3,4-difluorophthalic anhydride, 3,5-difluorophthalic anhydride, 3,6-difluorophthalic anhydride, 4,5-difluorophthalic anhydride, 3,4-dichlorophthalic anhydride, 3,5-dichlorophthalic anhydride, 3,6-dichlorophthalic anhydride, 4,5-dichlorophthalic anhydride, 3,4-dibromophthalic anhydride, 3,5-dibromophthalic anhydride, 3,6-dibromophthalic anhydride, 4,5-dibromophthalic anhydride, 3-chloro-4-fluorophthalic anhydride, 3-chloro-5-fluorophthalic anhydride, 3-chloro-6-fluorophthalic anhydride, 4-chloro-5-fluorophthalic anhydride, 3-bromo-4-fluorophthalic anhydride, 3-bromo-5-fluorophthalic anhydride, 3-bromo-6-fluorophthalic anhydride and 4-bromo-5-fluorophthalic anhydride.

The trihalogen-substituted phthalic anhydride is phthalic anhydride in which three hydrogen atoms of four hydrogen atoms contained in phthalic anhydride are substituted with a halogen atom.

Examples of the trihalogen-substituted phthalic anhydride include 3,4,5-trifluorophthalic anhydride, 3,4,6-trifluorophthalic anhydride, 3,4,5-trichlorophthalic anhydride, 3,4,6-trichlorophthalic anhydride, 3,4,5-tribromophthalic anhydride, 3,4,6-tribromophthalic anhydride, 3,4-dichloro-5-fluorophthalic anhydride, 3,4-dichloro-6-fluorophthalic anhydride and 4,5-dichloro-3-fluorophthalic anhydride.

The tetrahalogen-substituted phthalic anhydride is phthalic anhydride in which all four hydrogen atoms contained in phthalic anhydride are substituted with a halogen atom.

Examples of the tetrahalogen-substituted phthalic anhydride include tetrafluorophthalic anhydride, tetrachlorophthalic anhydride, tetrabromophthalic anhydride, 3,6-dichloro-4,5-difluorophthalic anhydride, 4,5-dichloro-3,6-difluorophthalic anhydride, 6-fluoro-3,4,5-trichlorophthalic anhydride and 6-chloro-3,4,5-trifluorophthalic anhydride.

Among these halogen-substituted phthalic anhydrides, monohalogen-substituted phthalic anhydride, dihalogen-substituted phthalic anhydride and trihalogen-substituted phthalic anhydride may further have a substituent which is inert for the below-mentioned reaction between a halogen-substituted phthalic anhydride and sodium borohydride. Examples of the substituent which is inert for the reaction between a halogen-substituted phthalic anhydride and sodium borohydride include alkyl groups having 1 to 12 carbon atoms, such as a methyl group, an ethyl group and a propyl group.

The halogen-substituted phthalic anhydride is preferably a tetrahalogen-substituted phthalic anhydride, and more preferably tetrachlorophthalic anhydride.

The halogen-substituted phthalic anhydride can be produced, for example, by a method of halogenating phthalic anhydride (see, for example, JP-A-6-329653), or a method in which a halogen-substituted phthalic acid is dehydrated by reacting with thionyl chloride or the like (see, for example, JP-A-6-16656).

The production method of the present invention includes a reaction step of reacting a halogen-substituted phthalic anhydride with sodium borohydride.

Sodium borohydride may be commercially available sodium borohydride, or may be one prepared by a known method in which a boric acid ester is reacted with sodium hydride.

Sodium borohydride tends to have low reactivity with moisture in atmospheric air and is easy to handle.

The use amount of sodium borohydride is preferably 0.5 mol or more, more preferably from 0.5 to 3 mol, and still more preferably from 0.7 to 1.5 mol, based on 1 mol of the halogen-substituted phthalic anhydride.

The reaction step is preferably performed in the presence of at least one solvent selected from the group consisting of ether solvents and alcohol solvents.

Examples of the ether solvent include diethylether, methyl tert-butylether, tetrahydrofuran, 1,4-dioxane, diisopropylether and 1,2-dimethoxyethane.

The ether solvent is preferably tetrahydrofuran or 1,2-dimethoxyethane, and more preferably 1,2-dimethoxyethane.

It is possible to use, as the ether solvent, a commercially available ether solvent as it is, or to use it after purifying by purification means such as distillation.

The use amount of the ether solvent is preferably from 0.1 to 100 parts by weight, and more preferably from 1 to 10 parts by weight, based on 1 part by weight of the halogen-substituted phthalic anhydride.

Examples of the alcohol solvent include compounds having at least one hydroxyl group, and specific examples thereof include methanol and an alcohol having 2 or more carbon atoms.

Examples of the alcohol having 2 or more carbon atoms include a primary alcohol having 2 to 12 carbon atoms, a secondary alcohol having 3 to 12 carbon atoms and a tertiary alcohol having 3 to 12 carbon atoms.

Examples of the primary alcohol having 2 to 12 carbon atoms include ethanol, 1-propanol, 1-butanol, 2-methyl-1-propanol, 1-pentanol, 2,2-dimethyl-1-propanol, benzyl alcohol, ethylene glycol, ethylene glycol monomethyl ether and ethylene glycol monoethyl ether.

Examples of the secondary alcohol having 3 to 12 carbon atoms include 2-propanol, 2-butanol, 2-pentanol, 3-pentanol, cyclopentyl alcohol and cyclohexyl alcohol.

Examples of the tertiary alcohol having 3 to 12 carbon atoms include 2-methyl-2-propanol, 2-methyl-2-butanol and 3-ethyl-3-pentanol.

The alcohol solvent is preferably methanol, a primary alcohol having 2 to 12 carbon atoms or a secondary alcohol having 3 to 12 carbon atoms, more preferably methanol, a primary alcohol having 2 to 6 carbon atoms or a secondary alcohol having 3 to 6 carbon atoms, still more preferably methanol or 2-propanol, and yet more preferably 2-propanol.

It is possible, to use, as the alcohol solvent, a commercially available alcohol solvent as it is, or to use it after purifying by purification means such as distillation.

The use amount of the alcohol solvent is preferably from 1 to 50 mol based on 1 mol of sodium borohydride when the alcohol solvent is methanol. When the alcohol solvent is an alcohol having 2 or more carbon atoms, the use amount thereof is preferably from 0.1 to 100 parts by weight, and more preferably from 1 to 10 parts by weight, based on 1 part by weight of the halogen-substituted phthalic anhydride.

In the reaction step, it is possible to allow a solvent, which is a solvent other than the alcohol solvent and ether solvent and does not exert an influence on the reaction between the halogen-substituted phthalic anhydride and sodium borohydride, to exist. Hereinafter, such a solvent may be sometimes referred to as an inert solvent.

Examples of the inert solvent include an aromatic hydrocarbon solvent, a halogenated aromatic hydrocarbon solvent and an aliphatic hydrocarbon solvent. Examples of the aromatic hydrocarbon solvent include toluene and xylene, examples of the halogenated aromatic hydrocarbon solvent include chlorobenzene and dichlorobenzene, and examples of the aliphatic hydrocarbon solvent include pentane, hexane, heptane, octane and cyclohexane. The inert solvent is preferably an aliphatic hydrocarbon solvent, more preferably an aliphatic hydrocarbon solvent having 5 to 10 carbon atoms, and still more preferably hexane. When the aliphatic hydrocarbon solvent is used as the inert solvent, it becomes easy to filter the obtained reaction mixed liquid and thus it is easy to recover the halogen-substituted phthalide.

It is possible to use, as the inert solvent, a commercially available inert solvent as it is, or to use it after purifying by purification means such as distillation.

There is no limitation on the use amount of the inert solvent, and the use amount is preferably from 0.05 to 10 parts by weight, more preferably from 0.1 to 2 parts by weight, and still more preferably from 0.2 to 0.5 parts by weight, based on 1 part by weight of at least one solvent selected from the group consisting of ether solvents and alcohol solvents.

The reaction step is performed by mixing a halogen-substituted phthalic anhydride with sodium borohydride, and there is no particular limitation on the mixing method. Examples of the mixing method include a method in which at least one solvent selected from the group consisting of ether solvents and alcohol solvents (hereinafter, this solvent is referred to as a "reaction solvent") is mixed with sodium borohydride and the obtained mixture is mixed with a halogen-substituted phthalic anhydride, and a method in which a reaction solvent is mixed with a halogen-substituted phthalic anhydride and the obtained mixture is mixed with sodium borohydride. In these mixing methods, each of sodium borohydride and the reaction solvent may be dividedly added. When sodium borohydride is used after preparation, for example, sodium borohydride can also be prepared in a mixture obtained by mixing a solvent with a halogen-substituted phthalic anhydride.

The reaction temperature in the reaction step is selected, for example, within a range from −20 to 200° C., preferably from 0 to 100° C., and more preferably from 10 to 80° C.

The reaction step is performed under a normal pressure, under reduced pressure or under pressurization, and is preferably performed under a normal pressure. The degree of progress of the reaction can be confirmed by analysis means such as gas chromatography or liquid chromatography.

It is preferred that the production method of the present invention further includes a mixing step of mixing the reaction mixture obtained in the reaction step with an acid. When the above reaction step is performed in the presence of the alcohol solvent, foaming is less likely to occur in the mixing step and thus it is easy to operate.

Examples of the acid include inorganic acids such as hydrogen chloride, sulfuric acid and boric acid; aliphatic carboxylic acids such as formic acid, acetic acid, trifluoroacetic acid, propionic acid, butanoic acid and oxalic acid; aromatic carboxylic acids such as benzoic acid; aliphatic sulfonic acids such as methanesulfonic acid, ethanesulfonic acid and trifluoromethanesulfonic acid; and aromatic sulfonic acids such as benzenesulfonic acid and p-toluenesulfonic acid. The acid is preferably an inorganic acid, and more preferably hydrogen chloride.

A commercially available acid can be used as the acid, and the acid may be used alone or as a mixture with a solvent such as water. Examples of the solvent to be mixed with the acid include the above alcohol solvent and ether solvent. When description is made by way of the case of hydrochloric acid as a mixture of hydrogen chloride and water as an example, hydrochloric acid containing 5 to 38% by weight of hydrogen chloride is preferred and hydrochloric acid containing 20 to 38% by weight of hydrogen chloride is more preferred.

There is no particular limitation on the use amount of the acid as long as the use amount is 0.5 mol or more based on 1 mol of sodium borohydride. The use amount is preferably 10 mol or less from the viewpoint of improving economical efficiency and volume efficiency.

In the mixing step, an inert solvent such as hexane may be further added to the reaction mixed liquid.

Specific examples of the mixing step include (I) a method in which a solvent such as water is mixed with an acid and the reaction mixture obtained in the reaction step is added in the obtained acid solution, and (II) a method in which an acid is added in the reaction mixture. Each of the above solvent, acid and acid solution may be dividedly added to the reaction mixture.

The temperature in the mixing step is usually selected within a range from 10 to 70° C.

It is also possible to taken out the halogen-substituted phthalide by optionally concentrating and/or treating the mixture obtained in the mixing step and subjecting it to solid-liquid separation such as filtration or decantation. It is also possible to subject the halogen-substituted phthalide thus taken out to washing with water and drying.

As a different embodiment, it is also possible to taken out the halogen-substituted phthalide by optionally subjecting the mixture obtained in mixing step to neutralization, and performing extraction and concentration.

It is also possible to purify the halogen-substituted anhydrous phthalide thus taken out by purification means such as recrystallization or column chromatography.

Examples of the halogen-substituted phthalide thus obtained include 4-fluoro-1(3H)-isobenzofuranone, 5-fluoro-1(3H)-isobenzofuranone, 6-fluoro-1(3H)-isobenzofuranone, 7-fluoro-1(3H)-isobenzofuranone, 4-chloro-1(3H)-isobenzofuranone, 5-chloro-1(3H)-isobenzofuranone, 6-chloro-1(3H)-isobenzofuranone, 7-chloro-1(3H)-isobenzofuranone, 4-bromo-1(3H)-isobenzofuranone, 5-bromo-1(3H)-isobenzofuranone, 6-bromo-1(3H)-isobenzofuranone, 7-bromo-1(3H)-isobenzofuranone, 4,5-difluoro-1(3H)-isobenzofuranone, 4,6-difluoro-1(3H)-isobenzofuranone, 4,7-difluoro-1(3H)-isobenzofuranone, 5,6-difluoro-1(3H)-isobenzofuranone, 4,5-dichloro-1(3H)-isobenzofuranone, 4,6-dichloro-1(3H)-isobenzofuranone, 4,7-dichloro-1(3H)-isobenzofuranone, 5,6-dichloro-1(3H)-isobenzofuranone, 4,5-dibromo-1(3H)-isobenzofuranone, 4,6-dibromo-1(3H)-isobenzofuranone, 4,7-dibromo-1(3H)-isobenzofuranone, 5,6-dibromo-1(3H)-isobenzofuranone, 4-chloro-5-fluoro-1(3H)-isobenzofuranone, 4-chloro-6-fluoro-1(3H)-isobenzofuranone, 4-chloro-7-fluoro-1(3H)-isobenzofuranone, 5-chloro-6-fluoro-1(3H)-isobenzofuranone, 4-bromo-5-fluoro-1(3H)-isobenzofuranone, 4-bromo-6-fluoro-1(3H)-isobenzofuranone, 4-bromo-7-fluoro-1(3H)-isobenzofuranone, 5-bromo-6-fluoro-1(3H)-isobenzofuranone, 4,5,6-trifluoro-1(3H)-isobenzofuranone, 4,5,7-trifluoro-1(3H)-isobenzofuranone, 4,5,6-trichloro-1(3H)-isobenzofuranone, 4,5,7-trichloro-1(3H)-isobenzofuranone, 4,5,6-tribromo-1(3H)-isobenzofuranone, 4,5,7-tribromo-1(3H)-isobenzofuranone, 4,5-dichloro-6-fluoro-1(3H)-isobenzofuranone, 4,5-dichloro-7-fluoro-1(3H)-isobenzofuranone, 5,6-dichloro-4-fluoro-1(3H)-isobenzofuranone, 4,5,6,7-tetrafluoro-1(3H)-isobenzofuranone, 4,5,6,7-tetrachloro-1(3H)-isobenzofuranone, 4,5,6,7-tetrabromo-1(3H)-isobenzofuranone, 4,7-dichloro-5,6-difluoro-1(3H)-isobenzofuranone, 5,6-dichloro-4,7-difluoro-1(3H)-isobenzofuranone, 7-fluoro-4,5,6-trichloro-1(3H)-isobenzofuranone, and 7-chloro-4,5,6-trifluoro-1(3H)-isobenzofuranone.

EXAMPLES

The present invention will be described in more detail by way of examples, but the present invention is not limited to these examples.

Example 1

<Reaction Step>

In a 300 mL flask equipped with a reflux condenser tube, 20.0 g of tetrachlorophthalic anhydride and 80 g of 2-propanol were charged at room temperature and the obtained mixture was cooled to 5° C. while stirring. To the mixture, 2.7 g of sodium borohydride was dividedly added (in four portions) over 1 hour. After completion of the addition, the mixture was heated to 40° C. and then stirred at the same temperature for 2 hours.

<Mixing Step>

The reaction mixture obtained in the reaction step was cooled to 5° C. and then 50.4 g of 5% hydrochloric acid was added to the cooled reaction mixture to obtain a mixture containing a white crystal precipitated therein. Foaming was scarcely confirmed. The mixture was filtrated, and then the white crystal taken out by filtration was washed with 50 g of water and dried to obtain 18.08 g of 4,5,6,7-tetrachloro-1(3H)-isobenzofuranone (hereinafter referred to as 4,5,6,7-tetrachlorophthalide) as a white crystal. The obtained white crystal is regarded as a first crop crystal. The filtrate was concentrated to dryness to obtain 0.91 g of a second crop crystal. The content of 4,5,6,7-tetrachlorophthalide of the respective crystals was determined by a gas chromatography internal standard method and a yield thereof was determined.

Content

First crop crystal: content of 4,5,6,7-tetrachlorophthalide: 98%

Second crop crystal: content of 4,5,6,7-tetrachlorophthalide: 44%

Yield

Total yield of first crop crystal and second crop crystal: 94% (based on tetrachlorophthalic anhydride)

Example 2

<Reaction Step>

In a 500 mL flask equipped with a reflux condenser tube, 40.0 g of tetrachlorophthalic anhydride, 150 g of 2-propanol and 50 g of hexane were charged at room temperature and the obtained mixture was cooled to 5° C. while cooling. To the mixture, 5.3 g of sodium borohydride was dividedly added (in four portions) over 1 hour. After completion of the addition, the mixture was heated to 40° C. and then stirred at the same temperature for 2 hours.

<Mixing Step>

The reaction mixture obtained in the reaction step was cooled to 5° C. and then 30 g of 35% hydrochloric acid was added to the cooled reaction mixture to obtain a mixture containing a white crystal precipitated therein. Foaming was scarcely confirmed. The white crystal was taken out by filtration of the mixture. The time required for filtration was less than one fourth as compared with the time required for filtration when the white crystal was taken out as the first crop crystal in Example 1. The filtered white crystal was washed with 100 g of water and dried to obtain 48.75 g of 4,5,6,7-tetrachlorophthalide as a white crystal. Using the obtained white crystal, the content of 4,5,6,7-tetrachlorophthalide of each crystal was determined by a gas chromatography internal standard method and a yield thereof was determined.

Content

Content of 4,5,6,7-tetrachlorophthalide: 73%

Yield

Yield: 93% (based on tetrachlorophthalic anhydride)

Example 3

<Reaction Step>

In a 200 mL flask equipped with a reflux condenser tube, 28.6 g of tetrachlorophthalic anhydride and 100 g of tetrahydrofuran were charged at room temperature and the obtained mixture was heated to 40° C. while stirring. Thereto, 3.8 g of sodium borohydride was dividedly added (in ten portions) over 4 hours. After completion of the addition, the mixture was stirred for 2 hours while keeping warm at 40° C.

<Mixing Step>

The reaction mixture obtained in the reaction step was cooled to room temperature. When one droplet of 5% hydrochloric acid was added to the cooled mixture, violent foaming was recognized. In a separate flask, 73 g of aqueous 5% hydrochloric acid was charged and the mixture was added dropwise thereto at room temperature. As a result, mild foaming was observed. The precipitated white crystal was filtered, and then the crystal taken out by filtration was washed with 2 g of cold tetrahydrofuran and dried to obtain 9.8 g of 4,5,6,7-tetrachlorophthalide as a white crystal. The obtained white crystal is regarded as a first crop, crystal. The filtrate was left to stand for 12 hours to further precipitate a crystal, and the precipitated crystal was subjected to the same operation as described above to obtain 14.0 g of a second crop crystal. The oily layer in the filtrate was collected and concentrated to obtain 3.0 g of a yellow oily product. The content of 4,5,6,7-tetrachlorophthalide in the respective crystals and oily product was determined by a gas chromatography internal standard method and a yield thereof was determined.

Content

First crop crystal: content of 4,5,6,7-tetrachlorophthalide: 93.6%

Second crop crystal: content of 4,5,6,7-tetrachlorophthalide: 92.8%

Oily product: content of 4,5,6,7-tetrachlorophthalide: 67%

Yield

Total yield of first crop crystal and second crop crystal: 82% (based on tetrachlorophthalic anhydride)

Total yield of first crop crystal, second crop crystal and oily product: 89% (based on tetrachlorophthalic anhydride)

Example 4

<Reaction Step>

In a 300 mL flask equipped with a reflux condenser tube, 28.6 g of tetrachlorophthalic anhydride and 80 g of 1,2-dimethoxyethane were charged at room temperature and the obtained mixture was stirred at 25° C. Thereto, 3.8 g of sodium borohydride was dividedly added (in three portions) over 30 minutes. Then, a mixed liquid of 6.4 g of methanol and 30 g of 1,2-dimethoxyethane was added dropwise at 25° C. to the mixture under stirring over 4 hours. During the dropwise addition, mild foaming was observed. After completion of the dropwise addition, the mixture was stirred for 2 hours while keeping warm at 25° C.

<Mixing Step>

To the reaction mixture obtained in the reaction step, 73 g of aqueous 5% hydrochloric acid was added dropwise over 30 minutes. During the dropwise addition, violent foaming was not recognized. The precipitated white crystal was filtered, and then the crystal taken out by filtration was washed with 5 g of cold 1,2-dimethoxyethane and dried to obtain 23.0 g of 4,5,6,7-tetrachlorophthalide as a white crystal. The obtained white crystal is regarded as a first crop crystal. The oily layer in the filtrate was collected and concentrated to obtain 4.0 g of a yellow oily product. The content of 4,5,6,7-tetrachlorophthalide in the crystal and oily product was determined by a gas chromatography internal standard method and a yield thereof was determined.

Content

First crop crystal: content of 4,5,6,7-tetrachlorophthalide: 99.4%

Oily product: content of 4,5,6,7-tetrachlorophthalide: 24%

Yield

Yield of first crop crystal: 84% (based on tetrachlorophthalic anhydride)

Total yield of first crop crystal and oily product: 88% (based on tetrachlorophthalic anhydride)

Example 5

<Reaction Step>

In a 300 mL flask equipped with a reflux condenser tube, 28.6 g of tetrachlorophthalic anhydride and 80 g of tetrahydrofuran were charged at room temperature and the obtained mixture was stirred at 25° C. Thereto, 3.8 g of sodium borohydride was dividedly added (in three portions) over 30 minutes. To the mixture under stirring at 25° C., a mixed liquid of 6.4 g of methanol and 30 g of tetrahydrofuran was added dropwise over 5 hours. During the dropwise addition, mild foaming was observed. After completion of the dropwise addition, the mixture was stirred for 2 hours while keeping warm at 25° C.

<Mixing Step>

To the reaction mixture obtained in the reaction step, 73 g of aqueous 5% hydrochloric acid was added dropwise over 30 minutes. During the dropwise addition, violent foaming was not recognized. The precipitated white crystal was filtered, and then the crystal taken out by filtration was washed with 3 g of cold tetrahydrofuran and dried to obtain 15.5 g of 4,5,6,7-tetrachlorophthalide as a white crystal. The obtained white crystal is regarded as a first crop crystal. The filtrate was ice-cooled to further precipitate a crystal and the precipitated crystal was subjected to the same operation as described above to obtain 8.0 g of a second crop crystal. The oily layer in the filtrate was collected and concentrated to obtain 3.5 g of a yellow oily product. The content of 4,5,6,7-tetrachlorophthalide in the respective crystals and oily product was determined by a gas chromatography internal standard method and a yield thereof was determined.

Content

First crop crystal: content of 4,5,6,7-tetrachlorophthalide: 99.95%

Second crop crystal: content of 4,5,6,7-tetrachlorophthalide: 67%

Oily product: content of 4,5,6,7-tetrachlorophthalide: 24%

Yield

Total yield of first crop crystal and second crop crystal: 77% (based on tetrachlorophthalic anhydride)

Total yield of first crop crystal, second crop crystal and oily product: 80% (based on tetrachlorophthalic anhydride)

Example 6

<Reaction Step>

In a 300 mL flask equipped with a reflux condenser tube, 28.6 g of tetrachlorophthalic anhydride and 60 g of tetrahydrofuran were charged at room temperature and the obtained mixture was stirred at 25° C. Thereto, 3.8 g of sodium borohydride was dividedly added (in three portions) over 30 minutes. Then, the mixture was stirred for 3 hours while keeping warm at 25° C.

<Mixing Step>

To the reaction mixture obtained in the reaction step under stirring at 25° C., a mixed liquid of 10 g of 35% hydrochloric acid (concentrated hydrochloric acid) and 50 g of tetrahydrofuran was added dropwise over 4 hours. During the dropwise addition, mild foaming was recognized. After completion of the dropwise addition, the mixture was stirred for 2 hours while keeping warm at the same temperature. Thereto, 73 g of water was added dropwise over 30 minutes. During the dropwise addition, violent foaming was not recognized. The precipitated white crystal was filtered, and then the crystal taken out by filtration was washed with 3 g of cold tetrahydrofuran and dried to obtain 16.3 g of 4,5,6,7-tetrachlorophthalide as a white crystal. The obtained white crystal is regarded as a first crop crystal. The filtrate was ice-cooled to precipitate a crystal and the precipitated crystal was subjected to the same operation as described above to obtain 1.0 g of a second crop crystal. The oily layer in the filtrate was collected and concentrated to obtain 10 g of a yellow oily product. The content of 4,5,6,7-tetrachlorophthalide in the respective crystals and oily product was determined by a gas chromatography internal standard method and a yield thereof was determined.

Content

First crop crystal: content of 4,5,6,7-tetrachlorophthalide: 99.7%

Second crop crystal: content of 4,5,6,7-tetrachlorophthalide: 90.6%

Oily product: content of 4,5,6,7-tetrachlorophthalide: 49%

Yield

Total yield of a first crop crystal and a second crop crystal: 63% (based on tetrachlorophthalic anhydride)

Total yield of a first crop crystal, a second crop crystal and an oily product: 81% (based on tetrachlorophthalic anhydride)

INDUSTRIAL APPLICABILITY

The present invention is useful as a method for producing a halogen-substituted phthalide which is an important compound as a raw material, an intermediate and a bulk of pharmaceuticals and pesticides.

The invention claimed is:

1. A method for producing 4,5,6,7-tetrachloro-1(3H)-isobenzofuranone, which comprises a reaction step of reacting tetrachlorophthalic anhydride with sodium borohydride, wherein a yield of the 4,5,6,7-tetrachloro-1(3H)-isobenzofuranone is at least 89%.

2. The method according to claim 1, wherein the reaction step is performed in the presence of at least one solvent selected from the group consisting of ether solvents and alcohol solvents.

3. The method according to claim 1, which further comprises a mixing step of mixing a reaction mixture obtained in the reaction step with an acid.

4. The method according to claim 3, wherein the acid is an inorganic acid.

5. The method according to claim 3, wherein the acid is hydrogen chloride.

* * * * *